United States Patent [19]

Mori et al.

[11] Patent Number: 6,072,074
[45] Date of Patent: Jun. 6, 2000

[54] PROCESS FOR PRODUCING 3-PROPYNYL-2-2-DIMETHYLCYCLOPROPHANE-CARBOXYLIC ACID AND ITS LOWER AKYL ESTERS

[75] Inventors: Tatsuya Mori, Toyonaka; Noritada Matsuo, Amagasaki, both of Japan

[73] Assignee: Sumitomo Chemical Company Limited, Osaka, Japan

[21] Appl. No.: 09/304,838

[22] Filed: May 5, 1999

[30] Foreign Application Priority Data

May 8, 1998 [JP] Japan .................................. 10-126025

[51] Int. Cl.[7] ........................... C07C 69/74; C07C 61/04; C07C 61/16
[52] U.S. Cl. ............................................. 560/124; 562/506
[58] Field of Search ............................... 560/124; 562/506

[56] References Cited

U.S. PATENT DOCUMENTS 3,853,952 12/1974 Kishida et al. .

FOREIGN PATENT DOCUMENTS

| 874515 | 8/1979 | Belgium . |
| 1 304 141 | 1/1973 | United Kingdom . |
| 1 304 144 | 1/1973 | United Kingdom . |
| 1304141 | 1/1973 | United Kingdom . |

OTHER PUBLICATIONS

J. Chem. Soc., 1970 Syntheses of 14C–Labelled (+)–trans–Chrysanthemum Mono–and Di–carboxylic Acids, and of Related Compounds, By L. Crombie et al, pp. 1076–1080.

*Primary Examiner*—Gary Geist
*Assistant Examiner*—Robert W. Deemie
*Attorney, Agent, or Firm*—Pillsbury Madison & Sutro LLP

[57] ABSTRACT

A propynyl compound shown by the formula:

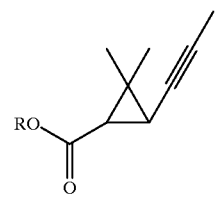

wherein R represents a lower alkyl group or a hydrogen atom, is an intermediate for producing 3-Z-(1-propenyl)-2,2-dimethylcyclopropanecarboxylic acid esters advantageously in industry.

2 Claims, No Drawings

PROCESS FOR PRODUCING 3-PROPYNYL-2-2-DIMETHYLCYCLOPROPHANE-CARBOXYLIC ACID AND ITS LOWER AKYL ESTERS

FIELD OF THE INVENTION

The present invention relates to propynyl compounds which are useful intermediates for producing pyrethroid compounds.

BACKGROUND ARTS

Prior, it has been known that certain ester compounds of 3-Z-(1-propenyl)-2,2-dimethylcyclopropanecarboxylic acid exhibit an excellent insecticidal effect in GB-1304141A. Further, the method described in the Scheme A below is known as a typical method for producing the ester of 3-Z-(1-propenyl)-2,2-dimethylcyclopropanecarboxylic acid (J.C.S. 1970, 1076).

Scheme A

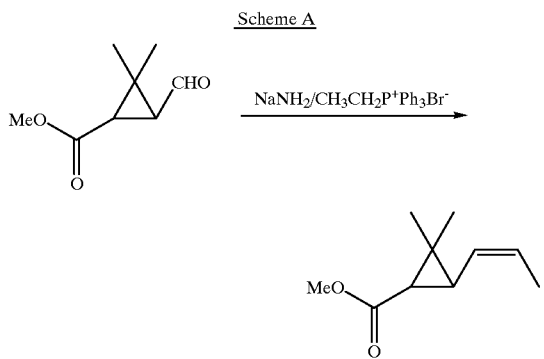

However, the above-mentioned method is not sufficient for industrially practical scale since it needs dangerous reagents, which are difficult to deal with in industry, such as alkali metal amides. Therefore, it is desired to develop an industrially advantageous method for producing 3-Z-(1-propenyl)-2,2-dimethylcyclopropanecarboxylic acid and its esters.

SUMMARY OF THE INVENTION

The present invention provides a useful intermediate compound and a method for producing 3-Z-(1-propenyl)-2,2-dimethylcyclopropanecarboxylic acid and esters.

That is, the present invention provides a propynyl compound (hereinafter referred as the present compound) shown in the formula (I):

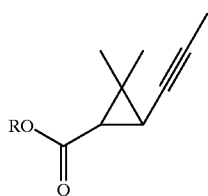

wherein R represents a $C_{1-4}$ alkyl group or a hydrogen atom, and a method for producing 3-Z-(1-propenyl)-2,2-dimethylcyclopropanecarboxylic acid or esters via the present compound.

DETAILED DESCRIPTION OF THE INVENTION

The present compound can be prepared, for example, by reacting a compound shown in the formula (II):

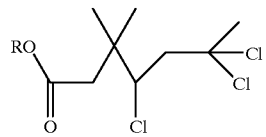

wherein R represents a $C_{1-4}$ alkyl group or a hydrogen atom, with a base.

The reaction is usually performed in a solvent. The range of the reaction time is usually within a range between 30 minutes and 96 hours and the range of the reaction temperature is usually within a range between 20° C. and a boiling point of the solvent used in the reaction or 150° C., preferably within a range between 40° C. and a boiling point of the solvent used in the reaction. The examples of the bases include amines such as 1,8-diazabicyclo[5.4.0]undec-7-ene (DBU); alkali metal alkoxides such as sodium methoxide, sodium ethoxide, potassium t-butoxide and sodium t-pentyloxide; alkali metal hydroxides such as sodium hydroxide and potassium hydroxide.

The ratio of the compound shown in the formula (II) and the base used is optionally set and preferably 3 to 10 mols of base are used per 1 mol of the compound shown in the formula (II).

The examples of the solvent include hydrocarbons such as benzene and toluene; ethers such as tetrahydrofuran; alcohols such as methanol and ethanol; dimethylformamide and the like.

The reaction solution after the reaction may be subjected to usual work-up procedures such as neutralization, extraction with organic solvent, concentration and so on for obtaining the present compound. Further, the present compound can be purified by chromatography, distillation and the like.

The compound shown in the formula (II) can be prepared, for example, according to the method described in Japanese unexamined patent publication No. sho-55-98141A. Said Japanese unexamined patent publication shows a preparation method of the compound shown in the formula (II) as an intermediate for producing 2,2-dimethyl-3-(2-halogeno-1-propenyl)cyclopropanecarboxylate.

The compound wherein R is a hydrogen atom in the present compound can be prepared by a hydrolysis reaction of the compound wherein R is a lower alkyl group in the present compound.

The reaction is usually performed in a solvent in the presence of water and either acid or base.

The range of the reaction time is usually within a range between 1 and 72 hours.

The range of the reaction temperature is usually within a range between 0° C. and a boiling point of the solvent used in the reaction, preferably within a range between 20° C. and a boiling point of the solvent used in the reaction.

The examples of the acids include inorganic acids such as hydrochloric acid and dilute sulfuric acid.

The examples of the bases include alkali metal hydroxides such as potassium hydroxide, sodium hydroxide and so on.

The examples of the solvents include alcohols such as methanol and ethanol; water; mixture thereof; and ethers containing water such as tetrahydrofuran containing water.

Equimolar to 2 moles of the acid or base is preferably used based on the starting compound.

The reaction solution after the reaction may be subjected to usual work-up procedures such as extraction with organic solvent, concentration and so on for obtaining the present compound. Further, the present compound can be purified by chromatography, recrystallization and so on.

Next, the methods for producing 3-Z-(1-propenyl)-2,2-dimethylcyclopropanecarboxylic acid (Compound(2)) and its lower alkyl ester (Compound(1)) are described.
(Method by the reaction route described in the Scheme B below)

Scheme B

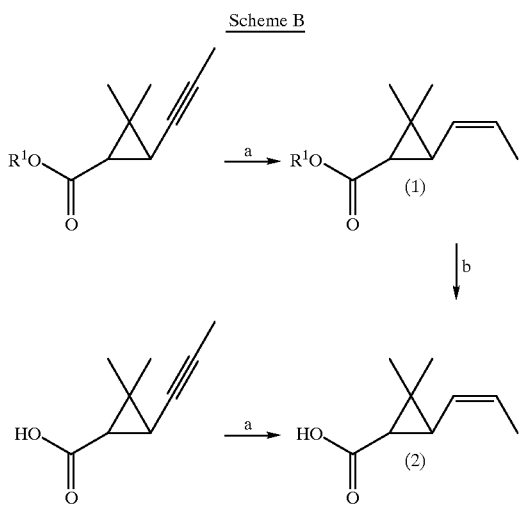

wherein $R^1$ represents a $C_{1-4}$ alkyl group.

The hydrogenation reaction a is usually performed in the presence of a catalyst in a solvent.

The range of the reaction time is usually within a range between 1 and 72 hours and the range of the reaction temperature is usually within a range between 0° C. and a boiling point of the solvent used in the reaction, preferably within a range between 20° C. and a boiling point of the solvent used in the reaction.

The examples of the catalyst of the hydrogenation include palladium-calcium carbonate catalyst (Lindlar catalyst) and so on.

The catalyst may be used in from 0.0001% by weight to the same weight, preferably from 0.001% by weight to 20% by weight based on the starting compound.

The examples of the solvents include hydrocarbons such as benzene, toluene and hexane; esters such as ethyl acetate; alcohols such as methanol and ethanol.

The reaction solution after the reaction may be subjected to usual work-up procedures such as concentration after filtering off the catalyst and so on for obtaining Compound (1) or Compound (2). Further, the compounds can be purified by chromatography, distillation and so on.

The hydrolysis reaction b is usually performed in the presence of water and either acid or base in a solvent.

The range of the reaction time is usually within a range between 1 and 72 hours.

The range of the reaction temperature is usually within a range between 0° C. and a boiling point of the solvent used in the reaction, preferably within a range between 20° C. and a boiling point of the solvent used in the reaction.

The examples of the acids include inorganic acids such as hydrochloric acid and dilute sulfuric acid.

The examples of the bases include alkali metal hydroxides such as potassium hydroxide and sodium hydroxide.

The examples of the solvents include alcohols such as methanol and ethanol; water; mixture thereof; and ethers containing water such as tetrahydrofuran containing water.

Equimolar to 2 moles of the acid or base is preferably used based on the starting compound.

The reaction solution after the reaction may be subjected to usual work-up procedures such as extraction with organic solvent, concentration and so on for obtaining Compound (2). Further, the compounds can be purified by chromatography, recrystallization and so on.

As mentioned above, the present invention also provides a method for producing 3-Z-(1-propenyl)-2,2-dimethylcycloprop anecarboxylic acid or $C_{1-4}$ alkyl ester which comprises (i) reacting a compound shown in the formula (II) with a base to have a propynyl compound shown in the formula (II), and (ii) allowing said propynyl compound to subject to hydrogenation reaction.

Compound (1) or Compound (2) can be derived to pyrethroid compounds according to the known methods described in Japanese examined patent publication No. sho-54-3933B and the like.

EXAMPLES

Hereinafter, the present invention is explained in more detail below referring to production example and reference examples but the present invention should not be limited in the following examples. Example 1 (preparation example of the present compound) A mixture solution of 27.5 g of ethyl 3,3-dimethyl-4,6,6-trichloroheptanoate and 204 g of a 20% ethanol solution of sodium ethoxide was stirred under reflux for 48 hours. The reaction solution was poured into ice and extracted with 500 ml of ethyl acetate 3 times. The combined extract was washed with 500 ml of water twice, dried over anhydrous sodium sulfate, concentrated under reduced pressure and the residue was distilled under reduced pressure to afford 11.6 g of ethyl trans-3-(1-propynyl)-2,2-dimethylcyclopropanecarboxylate (yield: 64%).

Boiling point: 70–80° C. (0.2 mmHg); $^1$H-NMR (CDCl$_3$, Internal standard: TMS) δ value (ppm): 1.18 (s,3H), 1.25 (s,3H), 1.30 (t,3H), 1.60 (d,1H), 1.80 (d,3H), 1.90 (dd,1H), 4.15 (q,2H)

Example 2 (preparation example of ethyl 3-Z-(1-propenyl)-2,2-dimethylcycloprop anecarboxylate)

To a mixture of 2.0 g of ethyl trans-3-(1-propynyl)-2,2-dimethylcyclopropanecarboxylate and 50 ml of hexane, 1 g of 5% palladium/calcium carbonate was added and the mixture was stirred vigorously for 8 hours at room temperature under hydrogen atmosphere. The catalyst was filtered off from the reaction mixture. A hexane solution (about 20 ml) obtained by washing the filtration product and about 50 ml of the filtrate were combined and concentrated under reduced pressure. The residue was purified by silica gel column chromatography to give 1.6 g of ethyl trans-3-Z-(1-propenyl)-2,2-dimethylcycloprop anecarboxylate (yield: 79%).

$^1$H-NMR (CDCl$_3$, Internal standard: TMS) δ value (ppm): 1.15 (s,3H), 1.30 (s,3H), 1.30 (t,3H), 1.45 (d,1H), 1.75 (d,3H), 2.15 (dd,1H), 4.10 (q,2H), 5.10 (m,1H), 6.0 (m,1H).

Reference Example (preparation example of 3-Z-(1-propenyl)-2,2-dimethylcycloprop anecarboxylic acid)

A mixture of 3.3 g of ethyl trans-3-Z-(1-propenyl)-2,2-dimethylcyclopropanecarboxylate, 0.8 g of sodium hydroxide, 12 ml of methanol and 6 ml of water was stirred under reflux for 2 hours. The reaction solution was poured into ice and the pH value of the solution was adjusted to 1 with 5% hydrochloric acid. The solution was extracted with 60 ml of ethyl acetate twice and the combined extract was washed with 40 ml of water twice, dried over anhydrous sodium sulfate and concentrated under reduced pressure to give 2.0 g of trans-3-Z-(1-propenyl)-2,2-dimethylcyclopropanecarboxylic acid (yield: 71%).

$^1$H-NMR (CDCl$_3$, Internal standard: TMS) δ value (ppm): 1.16 (s,3H), 1.32 (s,3H), 1.46 (d,1H), 1.71 (d,3H), 2.19 (d,1H), 5.14 (d,1H), 5.61 (d,1H).

What is claimed is:

1. A method for producing 3-Z-(1-propenyl)-2,2-dimethylcyclopropanecarboxylic acid or C$_{1-4}$ alkyl ester which comprises i) reacting a compound shown in the formula:

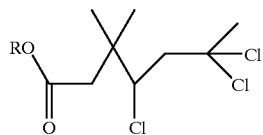

wherein R represents a C$_{1-4}$ alkyl group or a hydrogen atom, with a base to have a propynyl compound shown in the formula:

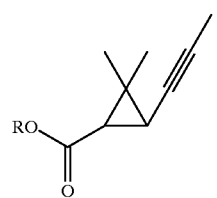

wherein R represents as defined above, and ii) allowing said propynyl compound to subject to hydrogenation reaction.

2. A method according to claim 1, wherein the hydrogenation reaction is performed in the presence of Lindlar catalyst.

* * * * *